(12) United States Patent
Da Silva Rodrigues et al.

(10) Patent No.: US 12,201,849 B2
(45) Date of Patent: Jan. 21, 2025

(54) PLANNING RADIATION THERAPY USING A PERSONALIZED HEMATOLOGIC RISK SCORE

(71) Applicant: Elekta Inc., Atlanta, GA (US)

(72) Inventors: Pedro Jorge Da Silva Rodrigues, Veldhoven (NL); Maria Luiza Bondar, Waalre (NL); Andreia Maria Araujo Trindade Rodrigues, Veldhoven (NL); Vanda Lucia De Carvalho Vittorino De Almeida, Veldhoven (NL)

(73) Assignee: Elekta Inc., Atlanta, GA (US)

( * ) Notice: Subject to any disclaimer, the term of this patent is extended or adjusted under 35 U.S.C. 154(b) by 181 days.

(21) Appl. No.: 17/786,659

(22) PCT Filed: Dec. 15, 2020

(86) PCT No.: PCT/EP2020/086060
§ 371 (c)(1),
(2) Date: Jun. 17, 2022

(87) PCT Pub. No.: WO2021/130047
PCT Pub. Date: Jul. 1, 2021

(65) Prior Publication Data
US 2023/0021147 A1    Jan. 19, 2023

(30) Foreign Application Priority Data

Dec. 23, 2019 (EP) ..................................... 19219251

(51) Int. Cl.
*A61N 5/10* (2006.01)
*G16H 20/40* (2018.01)

(52) U.S. Cl.
CPC ........... *A61N 5/1031* (2013.01); *G16H 20/40* (2018.01)

(58) Field of Classification Search
CPC .............................. A61N 5/1031; G16H 20/40
See application file for complete search history.

(56) References Cited

U.S. PATENT DOCUMENTS

| | | | | |
|---|---|---|---|---|
| 2016/0129282 | A1* | 5/2016 | Yin | ........................ G16H 40/20 600/1 |
| 2017/0259083 | A1* | 9/2017 | Nakatsugawa | ...... A61N 5/1049 |

FOREIGN PATENT DOCUMENTS

| | | |
|---|---|---|
| EP | 3842097 | 6/2021 |
| WO | 2021130047 | 7/2021 |

OTHER PUBLICATIONS

PCT International Search Report, International application No. PCT/EP2020/086060, Feb. 12, 2021.

(Continued)

*Primary Examiner* — Courtney D Thomas
(74) *Attorney, Agent, or Firm* — Schwegman Lundberg & Woessner, P.A.

(57) ABSTRACT

Thereto a method and a system for planning radiation therapy are provided, as well as an arrangement for radiation therapy planning and a computer program product for carrying out the method. For planning the radiation therapy, the following steps are performed. Patient data of a subject to be treated is received as well as image data of the subject to be treated. The image data comprises anatomical image data of one or more organs at risk associated with the functioning of the immune system. Next, the patient 122 data and the image data are processed to obtain a risk score for the one or more organs at risk associated with the functioning of the immune system. The risk score is indicative of the risk of hematologic toxicity in the subject to be treated in response to the radiation therapy. Then the radiation therapy treatment is planned using the obtained risk score.

15 Claims, 7 Drawing Sheets

(56) References Cited

OTHER PUBLICATIONS

Fleming C. et al., "Normal Tissue Considerations and Dose-Volume Constraints in the Moderately Hypofractionated Treatment of Non-Small Cell Lung Cancer", Radiotherapy and Oncology, vol. 119, No. 3, pp. 423-431, Jun. 2016.
Braley J. D. et al., "Sandard-Dose Versus High-Dose Conformal Radiotherapy with Concurrent and Consolidation Carboplatin Plus Paclitaxel with or without Cetuximab for Patients with Stage IIIA or IIIB Non-Small-Cell Lung Cancer (RTOG 0617): A Randomised, Two-by-Two Factorial Phase 3 Study", Lancet Oncology, vol. 16, No. 2, pp. 187-199, Feb. 2015.
Pike L. R. G. et al, "The Impact of Radiation Therapy on Lymphocyte Count and Survival in Metastatic Cancer Patients Receiving PD-1 Immune Checkpoint Inhibitors", International Journal of Radiation Oncology, Biology, Physics, vol. 103, No. 1, pp. 142-151, Jan. 2019.
Weinreich M. A. et al., "Thymic Emigration: When and How T Cells Leave Home, ", Journal of Immunology, Baltimore, MD, vol. 181, No. 4, pp. 2265-2270, Aug. 2008.
Rezzani R. et al., "Thymus and Aging: Morphological, Radiological, and Functional Overview", AGE, vol. 36, No. 1, pp. 313-351, Feb. 2014.
Lepletier A. et al., "Inflammation and Thymus Ageing", Frontiers of Hormone Research, vol. 48, pp. 19-36, 2017.
Sun D.-P. et al., "Thymic Hyperplasia After Chemotherapy in Adults with Mature B Cell Lymphoma and its Influence on Thymic Output and CD4+ T Cells Repopulation", Oncoimmunology, vol. 5, No. 5, Feb. 2016.
Sfikakis P. P. et al., "Age-Related Thymic Activity in Adults Following Chemotherapy-Induced Lymphopenia", European Journal of Clinical Investigation, vol. 35, Issue 6, pp. 380-387, 2005.
Ito R. et al., "Late Effects of Exposure to Ionizing Radiation and Age on Human Thymus Morphology and Function", Radiation Research, vol. 187, No. 5, pp. 589-598, 2017.
Dong P. et al., "4π Noncoplanar Stereotactic Body Radiation Therapy for Centrally Located or Larger Lung Tumors", International Journal of Radiation Oncology, Biology and Physics, vol. 86, No. 3, pp. 407-413, Jul. 2013.
Wu K. et al., "Statistical Atlas-Based Morphological Variation Analysis of the Asian Humerus: Towards Consistent Allometric Implant Positioning", International Journal of Computer Assisted Radiology and Surgery, vol. 10, No. 3, pp. 317-327, Mar. 2015.
Abravan A. et al., "Mapping Bone Marrow Response in the Vertebral Column by Positron Emission Tomography Following Radiotherapy and Erlotinib Therapy of Lung Cancer", Molecular Imaging and Biology, vol. 21, pp. 391-398, 2018.
Tsujikawa T. et al., "18F-FLT PET/MRI for Bone Marrow Failure Syndrome—Initial Experience", EJNMMI Research, vol. 9, No. 1, Feb. 2019.
Leimgruber A. et al., "Effect of Platinum-Based Chemoradiotherapy on Cellular Proliferation in Bone Marrow and Spleen, Estimated by 18-FFLT PET/CT in Patients with Locally Advanced Non-Small Cell Lung Cancer", Journal of Nuclear Medicine, vol. 55, pp. 1075-1080, 2014; 2014.
Hyer D.E. et al., "Estimation of Organ Doses from Kilovoltage Cone-Beam CT Imaging Used During Radiotherapy Patient Position Verification", Medical Physics, vol. 37, No. 9, pp. 4620-4626, Sep. 2010.
Pyone Y.Y. et al., "Determination of Effective Doses in Image-Guided Radiation Therapy System", Journal of Physics: Conference Series, vol. 694, p. 012007, 2016.
Nasseri F. et al., "Clinical and Radiologic Review of the Normal and Abnormal Thymus: Pearls and Pitfalls", RadioGraphics, vol. 30, No. 2, pp. 413-418, 2010.
Viglianti B.L. et al., "Common Pitfalls in Oncologic FDG PET/CT Imaging", Journal of American Osteopathic College of Radiology, vol. 7, Issue 1, 2018.
McGuire S.M. et al., "[18F]FLT PET Quantification of Bone Marrow Response to Radiation Dose", International Journal of Radiation, Oncology, Biology, Physics, vol. 81, No. 3, pp. 888-893, Nov. 2012.
Scarlli M. et al., "FLT PET/CT Imaging of Metastatic Prostate Cancer Patients Treated with pTVG-HP DNA Vaccine and Pembrolizumab", Journal for Immunotherapy of Cancer, vol. 7, issue 1, pp. 23, Jan. 2019.
Kuncman L. et al., "Bone Marrow Sparing RT in Era of Immunotherapy", Journal of Oncology 2017, vol. 67, No. 5, pp. 301-307, 2017.
Aide N. et al., "FDG PET/CT for Assessing Tumour Response to Immunotherapy", European Journal of Nuclear Medicine ad Lolecular Imaging, vol. 46, p. 238-250, 2019.
"European Application Serial No. 19219251.6, Extended European Search Report mailed May 28, 2020", 6 pgs.
"European Application Serial No. 19219251.6, Noting of Loss of Rights mailed Jan. 25, 2022", 2 pgs.
"International Application Serial No. PCT EP2020 086060, Written Opinion mailed Feb. 12, 2021", 5 pgs.
"International Application Serial No. PCT EP2020 086060, International Preliminary Report on Patentability mailed Jul. 7, 2022", 7 pgs.

\* cited by examiner

400

| | 401 | 402 | 403 |
|---|---|---|---|
| P1 | M | L | L |
| P2 | M | L | M |
| P3 | M | H | M |

| | 551 | 552 | 553 |
|---|---|---|---|
| P1 | 0.5 | 1 | - |
| P2 | 0.5 | 1.4 | ++ |
| P3 | 0.5 | 0.5 | -- |

FIG. 4b

|  | 715 | 720 | 725 |
|---|---|---|---|
| OARIS1 | 0.9 | L | H |
| OARIS2 | 0.9 | H | M |
| OARIS3 | 0.3 | H | H |
| OARIS4 | 0.3 | M | M |

PLANNING RADIATION THERAPY USING A PERSONALIZED HEMATOLOGIC RISK SCORE

CROSS-REFERENCE TO RELATED APPLICATIONS

This patent application claims the priority benefit under 35 U.S.C. § 371 of International Patent Application no. PCT/EP2020/086060, filed Dec. 15, 2020, which claims the benefit of European Patent Application No. EP19219251.6, filed on Dec. 23, 2019. These applications are hereby incorporated by reference herein in their entirety.

FIELD OF THE INVENTION

The invention generally relates to planning radiation therapy. In particular, but not exclusively, the invention relates to planning radiation therapy taking into account the risk of hematologic toxicity occurring in the subject in response to the radiation therapy.

BACKGROUND OF THE INVENTION

In radiation therapy, target structures (TSs) in patient's bodies, such as tumors, are treated by subjecting them to radiation. The radiation can be in the form of external radiation such as photons, or particles such as protons, for example in external beam radiotherapy. Radiation therapy (RT) treatment aims to kill cancer cells by delivering high doses of radiation to the tumor. Inevitably, RT delivers doses to the normal tissue, which can lead to side effects. Therefore conventionally treatment is delivered in such a way that the radiation that is delivered to the TSs is as high as possible, while at the same time the radiation delivered to the surrounding healthy tissue and structures, usually referred to as organs at risk (OARs), is as low as possible.

A common side effect is the occurrence of hematological toxicities (HT). For example, rapid and severe lymphopenia, which is a reduction of blood circulating lymphocytes, occurs in 50% of patients within 30-days that undergo RT.

HTs are a measure of the status of the immune system. Low lymphocyte count is negatively associated with poor survival. Also absolute lymphocyte count is positively associated with the response to immunotherapy. For an effective tumor control and for coupling with other therapies such as checkpoint inhibitor immunotherapies, the immune system, and in particular lymphocyte T-cell subpopulations need to be preserved.

A problem in the current RT practice is that, the organs associated with the functioning of the immune system, such as the thymus, areas of active bone marrow, the vertebrae, and large blood vessels are rarely even taken into account as OARs. And even when they are, depending on the location of the tumor, strict dose limits for the different OARs associated with the functioning of the immune system can be difficult to obtain in conventional radiotherapy plan optimization, especially for photon radiotherapy delivery. Strict dose limits are particularly difficult to obtain for the thymus, which is located in the heart region.

Furthermore, a conventional intensity modulated radiation therapy approach guided by anatomic organs delineation may impose significant constraints in the radiotherapy plan optimization leading to an increase in complexity and computing time to generate the plan. In addition, a priori it is not known how the best possible sparing could be achieved.

Better tissue sparing can be obtained by non-coplanar beam arrangements or by using proton therapy. However, these types of radiation therapy treatment requires special equipment, and are more expensive than conventional coplanar photon deliveries.

As a consequence, often in conventional treatments the OARs associated with the functioning of the immune system are exposed to dose levels which exceed the radio sensitivity thresholds.

SUMMARY OF THE INVENTION

The current invention seeks to provide an approach to radiation therapy planning wherein the OARs associated with the functioning of the immune system are taken into account for the purpose of reducing the risk of occurrence of HT. The current invention further seeks to address the need for physicians to have a risk score for HT occurring in RT for individual patients.

Thereto a method and a system for planning radiation therapy are provided, as well as an arrangement for radiation therapy planning and a computer program product for carrying out the method.

The method for planning radiation therapy comprises a step of receiving patient data of a subject to be treated and a step pf receiving image data of the subject to be treated. The image data comprises anatomical image data of one or more organs at risk associated with the functioning of the immune system. The method further comprises a step of processing the patient data and the image data to obtain a risk score for the one or more organs at risk associated with the functioning of the immune system. The risk score is indicative of the risk of HT in the subject to be treated in response to the radiation therapy. The method also further comprises a step planning a radiation therapy treatment using the obtained risk score to reduce the risk of hematologic toxicity in the subject to be treated.

The one or more organs at risk associated with the functioning immune system can, for example, be one or more of: the thymus, an area of active bone marrow, vertebra, the heart, the heart chambers, or a large blood vessel.

Preferably, the image data of the subject further includes functional image data for the one or more organ at risk associated with the functioning of the immune system, and wherein the risk score is obtained by applying a functional model of the organs at risk. An advantage of including function image data is that highly functional regions of the immune system organs such as e.g., active bone marrow, and thymus tissue can be identified and sparing for these regions may be improved when the risk score for such an area is high.

Preferably, the risk score is obtained by applying a model based on historic patient data. Additionally or alternatively, the patient data may comprise blood cell counts in the subject, in particular lymphocyte counts in the subject. Information of blood cell counts such as lymphocyte counts can be of particular relevance when it is envisioned to treat the patient further with a form of immunotherapy.

In a preferred embodiment, planning the radiation therapy treatment comprises selecting a type of radiation therapy, e.g one of intensity modulated radiation therapy, volumetric modulated radiation therapy, photon radiation therapy with a non-coplanar beam arrangement, or particle therapy such as proton therapy; and calculating a radiation therapy plan for the selected type of radiation therapy. This has the advantage of allowing the physician to select expensive therapies involving lengthy and complex planning procedures such as proton therapy and non-coplanar radiation therapy for those cases that will have the highest benefit from their additional sparing options. More conventional photon radiation treatment, such as VMAT, can be selected for cases where the risk is within acceptable boundaries.

In another preferred embodiment, that may be combined with other embodiments and preferences, the image data further comprises anatomical image data of at least a target structure, and the method further comprises receiving clinical goals for the target structure and the one or more organs at risk.

It is an additional possibility to adjust the clinical goals using the obtained risk score when planning the radiation therapy treatment.

In a further aspect, planning the radiation therapy treatment may comprises calculating organ sparing probability scores for the one or more organs at risk associated with the functioning of the immune system for each of a group of possible radiation therapy treatment options. This can be particularly advantageous when the radiation therapy treatment options are different geometric beam arrangements in intensity modulated radiation therapy.

The system for planning radiation therapy comprises an input for receiving patient data of a subject to be treated, and an input for receiving image data of the subject to be treated. The image data comprises anatomical image data of at least one organ at risk associated with the functioning of the immune system. The system further comprises a risk score calculation unit and a radiation therapy planning unit. The risk score calculation unit is configured to process the patient data and the image data to obtain a risk score for one or more organs at risk associated with the functioning of the immune system indicative of the risk of HT in the subject to be treated in response to the radiation therapy. The radiation therapy planning unit is configured to select a radiation therapy plan using the obtained risk score to reduce the risk of hematologic toxicity in the subject to be treated.

In an embodiment the system further comprises a display unit configured to display the risk score of the at least one organ at risk. Preferably, the display is further configured to display organ sparing probability scores for the organs at risk associated with the functioning of the immune system for each group of possible radiation therapy options.

Such an embodiment has the advantage of providing the physician or planning technologist with a convenient overview to provide information and/or assist in taking decisions regarding the treatment planning.

The arrangement for radiation therapy planning comprises one or more imaging devices configured to generate image data of a subject to be treated, a patient information database configured to store and provide patient data, and the system as described above for planning radiation therapy.

Further aspects are described with reference to the appended claims and the exemplary embodiments.

An advantage of the current invention is that the risk of the occurrence of hematological toxicities due to radiation therapy can be reduced. Hereby it may be possible to provide better treatment results for patients in general and for patients undergoing combined radiation therapy with immunotherapy in particular.

Another advantage is that more personalized clinical goals can be prescribed by the physician in planning of the radiation therapy.

A further advantage is that better sparing of organs at risk associated with the functioning of the immune system can be achieved.

Another advantage lies in that constraints for organs at risk associated with the functioning of the immune system can be prioritized and unnecessarily strict constraints avoided, thereby providing for more efficient radiation therapy plan calculation.

BRIEF DESCRIPTION OF THE DRAWINGS

In the following drawings:

FIGS. 4a and 4b schematically illustrate examples of displays showing risk scores for organs at risk associated with the functioning of the immune system.

DETAILED DESCRIPTION OF THE INVENTION

Figure 1:
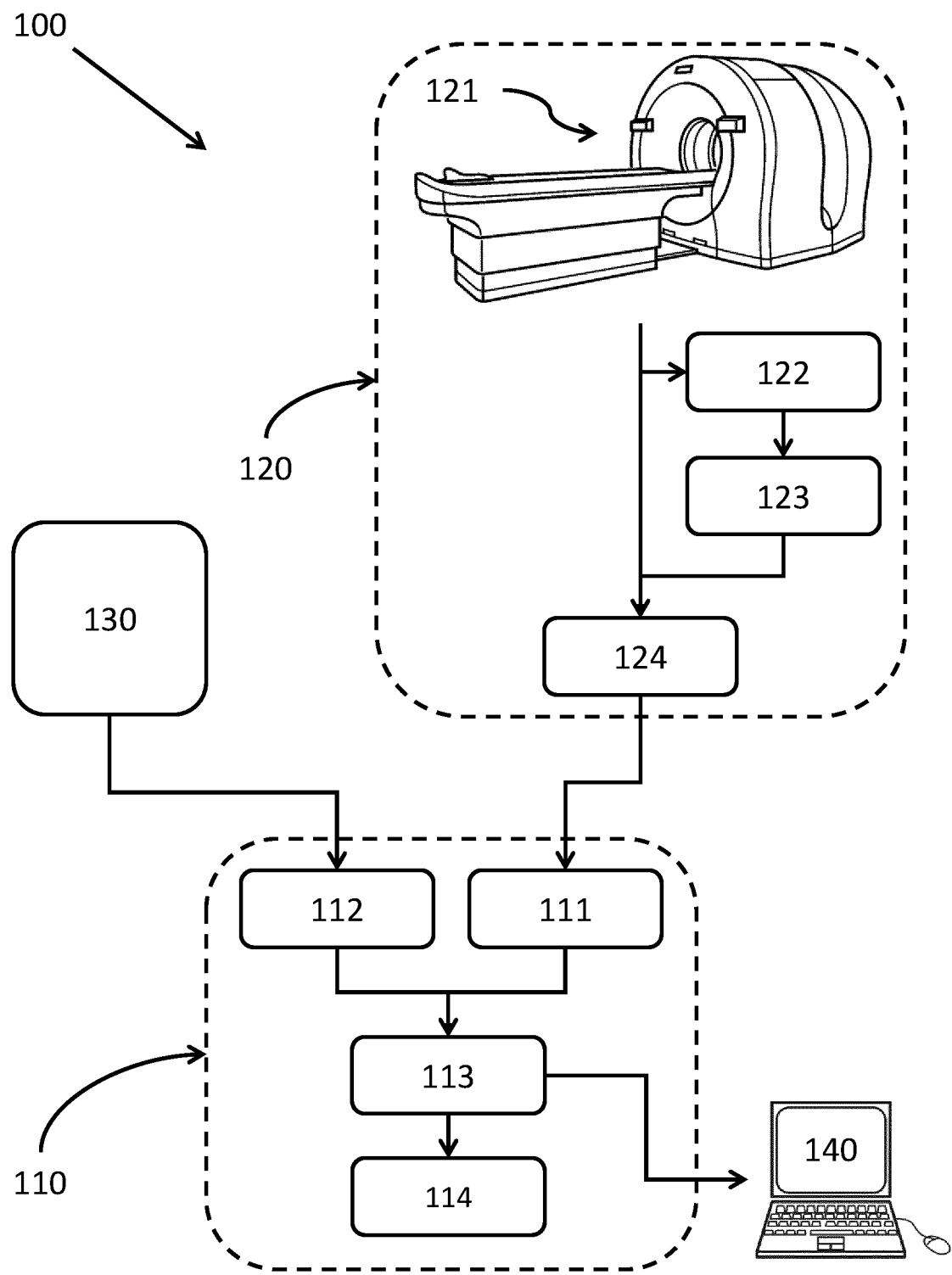
FIG. 1 schematically and exemplarily illustrates a system for planning radiation therapy and further components of an arrangement for planning radiation therapy.

FIG. 1 illustrates a system for planning radiation therapy 110. In this example, the system is illustrated as part of an arrangement 100 for planning radiation therapy. In addition to the system for planning radiation therapy 110, the arrangement comprises an imaging device 120 and a patient information database 130.

The imaging device 120 is configured to generate image data of the subject. Imaging device 120 may be a single unit for medical imaging, but there can also be more imaging devices to obtain the data. The acquired image can be a computed tomography image (CT), magnetic resonance image (MR), positron emission tomography (PET) image, another medical image, or a combined image, such as a combined PET/CT or PET/MR image. In FIG. 1, as an example, a combined PET/CT imaging device 121 is illustrated. In the image, at least one organ at risk associated with the funtioning of the immune system (OARIS) is delineated using a contouring tool 122 to provide anatomical image data 123 for the OARIS. Normally, the regions of interest in the subject will comprise at least one target structure (TS), normally a tumor, and may also include more OARISs and other OARs. Preferably all TS, OARISs and OARs are delineated to provide their anatomical image data. A contouring tool such as 122 commonly interacts with the user, who can be for example a trained medical imaging technologist or a radiologist, to define the contours of the regions of interest. This process can be completely manual, or partly or fully automated.

The anatomic image data 123 may be combined with further image data that can be used in planning the RT. Preferably the image data also comprises functional image data obtained from e.g. a PET or SPECT imaging device. The image data 124 can be available directly to the planning system 110 as illustrated here, but is more commonly stored in a database such as a picture archiving system (PACS) or hospital information system (HIS) to provide more convenient access.

The patient information database 130 is configured to store and provide patient data. Typically patient data is stored in an electronic medical record (EMR). This data can be any data previously collected and stored regarding the subject to be treated. The data can be personal data such as gender, age, height or weight. The data can also be medical data such as a blood panel and baseline lymphocyte counts or information on side effects that occurred in previous treatments.

The system for planning RT 110 has an input 111 for receiving patient data of a subject to be treated, and an input 112 for receiving image data of the subject to be treated. In this example, the patient data is received fully automatically from patient information database 130. Alternatively, the data can be entered manually, or partially entered manually and partially received from database 130. The received image data 124 comprises anatomical image data 123 of at least one OARIS. RT planning system 110 further comprises a risk score calculation unit 113 and a radiation therapy planning unit 114. The risk score calculation unit is configured to process the patient data and the image data to obtain a risk score for one or more OARISs indicative of the risk of HT in the subject to be treated in response to the radiation therapy. When the image data includes functional image data, the risk score is preferably a functional risk score that is obtained by using this data. The risk score can for example be obtained by applying a functional model of the OARIS. In the example of FIG. 1, the arrangement also comprises an optional display unit 140 configured to display the risk score of the at least one OARIS.

The radiation therapy planning unit 114 is configured plan a radiation therapy treatment using the obtained risk score. Planning the RT treatment may proceed automatically based on pre-defined criteria, but could also be done interactively by the user. The user of the system will typically be a radiation oncologist or a radiotherapy planning technologist. For example, planning a radiation therapy treatment can comprises selecting a type of radiation therapy, e.g one of intensity modulated radiation therapy (IMRT), volumetric modulated radiation therapy (VMAT), photon radiation therapy with a non-coplanar beam arrangement, or particle therapy such as proton therapy; and calculating a radiation therapy plan for the selected type of radiation therapy.

Calculating and optimizing an RT treatment plan is commonly an interactive process with the user. To enable this, the RT planning unit 110 advantageously has a user interface, which is preferably a graphical user interface (GUI). Display 140 can be integrated with such a GUI.

Figure 2:
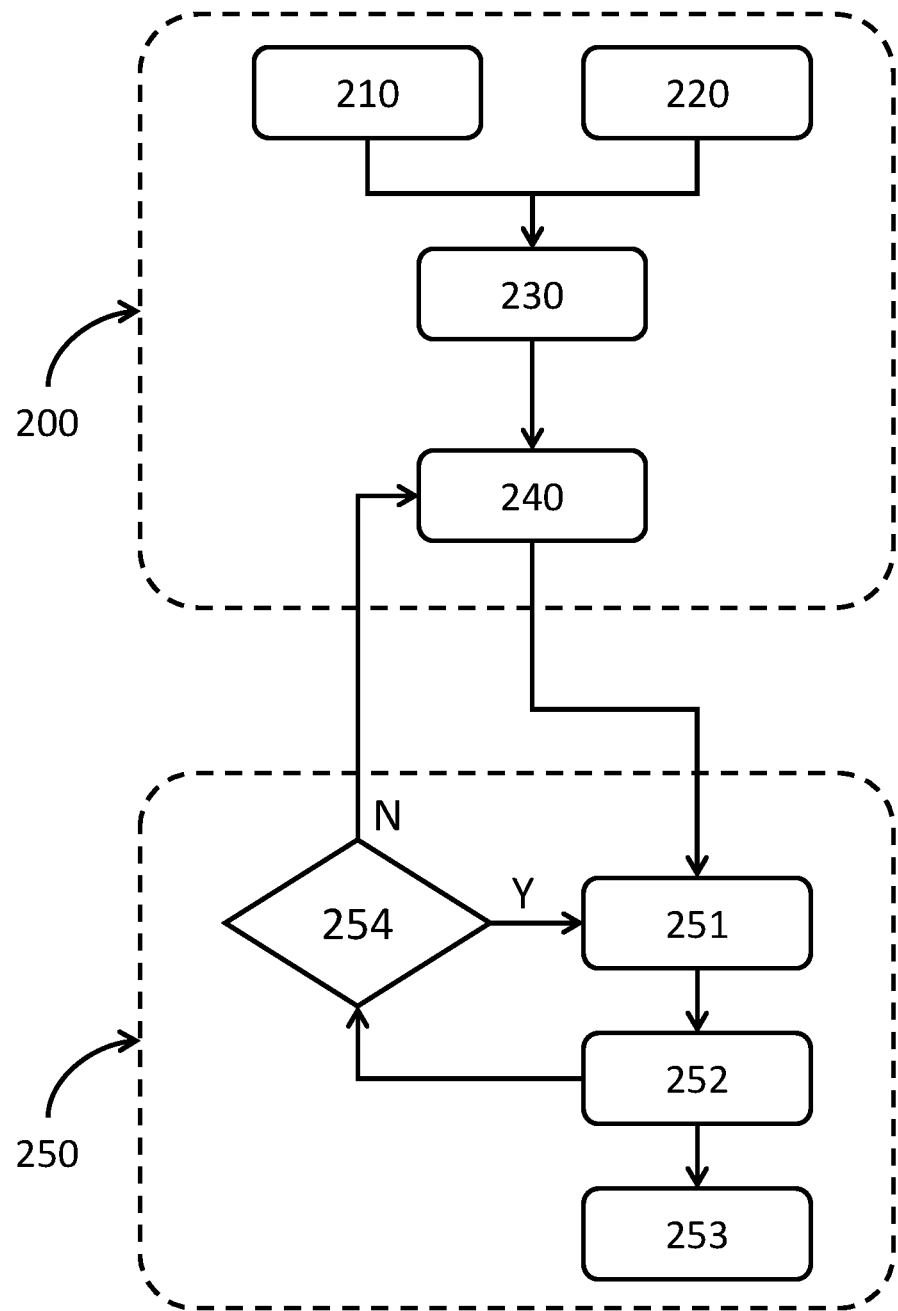
FIG. 2 schematically illustrates an example of a method for planning radiation therapy.

FIG. 2 schematically illustrates steps of a method for planning radiation therapy 200. The method for planning radiation therapy is followed by additional method steps 250 for adapting the RT plan during the course of treatment.

The method for planning RT 200 comprises a step of receiving patient data of a subject to be treated 210 and a step pf receiving image data of the subject to be treated 220. The image data comprises anatomical image data of one or more OARISs. The image data may be generated as described above in relation to the imaging device 120. The method further comprises a step of processing the patient data and the image data to obtain a risk score 230 for the one or more OARISs. The risk score is indicative of the risk of HT in the subject to be treated in response to the radiation therapy. The method also further comprises a step planning a RT treatment 240 using the obtained risk score.

In an optional addition to the method 250, the subject to be treated may be monitored during the treatment to determine if the risk of HT remains within acceptable limits. If this is not the case, a physician may decide to adapt the treatment accordingly or take additional measures to alleviate side effects of the treatment.

In the method for planning RT 200, risk scores for the one or more OARISs are calculated before the RT treatment is administered (pre-treatment). RT treatment is usually administered in several instances called fractions with a recovery period between each fraction. Each fraction can have an impact on the risk score of each OARIS. In the additional method, at step 251 an RT fraction is delivered to the subject. After delivery, the risk score for the one or more OARISs is updated 252 to determine the current risk of HT. The updated score is determined in a similar manner as is done at step 230, but based on updated patient data and/or updated image data. Updated image data can be derived from e.g. the setup image taken immediately prior to treatment delivery, or an additionally scheduled image. For patients treated with hybrid system combining MRI or PET imaging with a radiotherapy delivery device the update functional image can be acquired prior to treatment delivery at the hybrid unit. Updated patient data can e.g. be an updated blood panel or updated lymphocyte count.

The series of updated scores can be used to monitor the subject during therapy and post treatment 253. An advantageous additional option is to check each updated risk score to determine if the risk of HT occurring as a result of continued treatment is still within acceptable limits 253. If this is the case, indicated with Y, the treatment can proceed to the next fraction. If the HT risk is too high, indicated with N, the physician can decide to return to planning the treatment 240, but now using the updated risk score.

Figure 3:
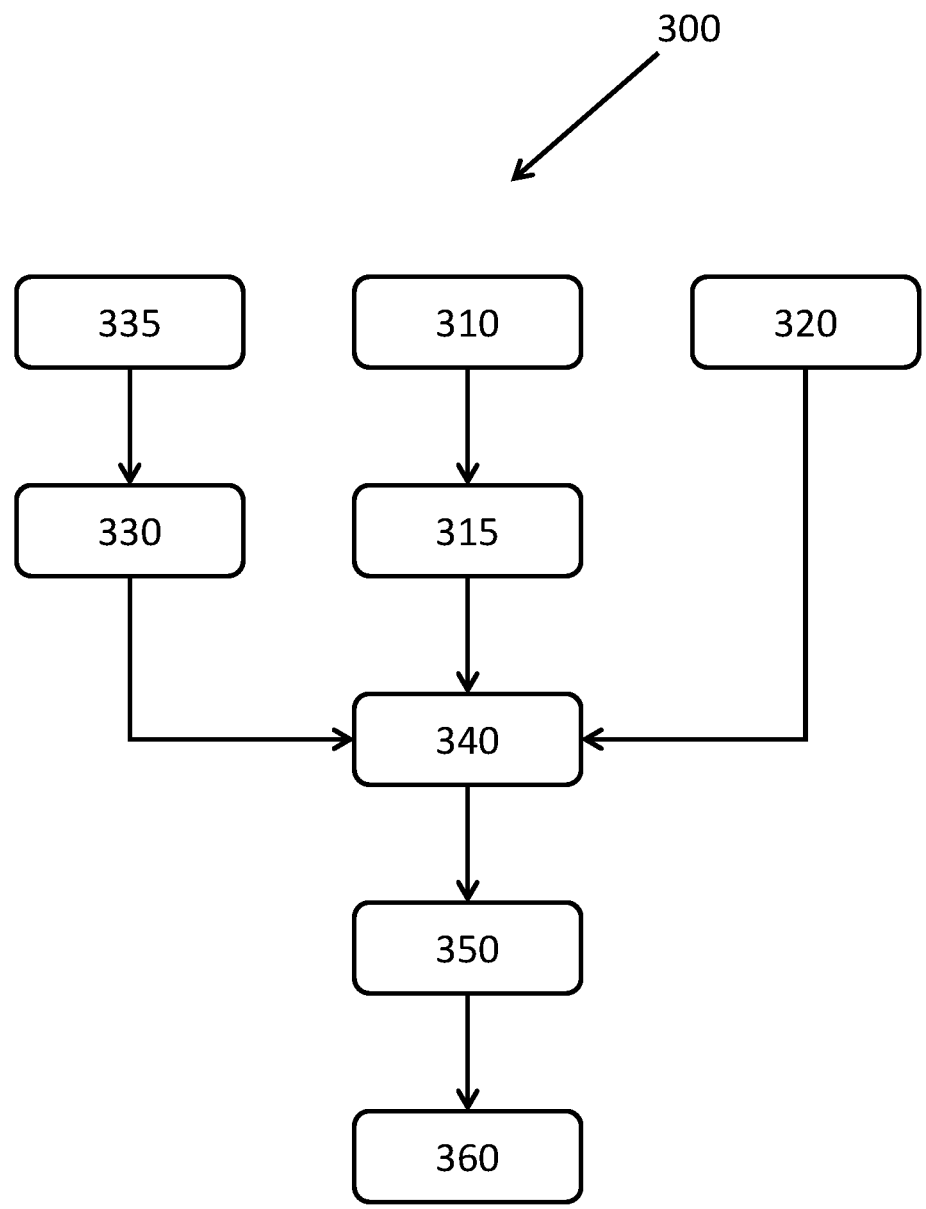
FIG. 3 schematically illustrates an example of processing the patient data and the image data to obtain a risk score for an organs at risk associated with the functioning of the immune system.

FIG. 3 illustrates an example of processing the patient data and the image data to obtain a risk score for an OARIS 300. In this example, a risk score is calculated for the thymus.

The primary function of the thymus, which is located at the base of the heart, is to promote the differentiation of bone marrow derived lymphocyte progenitors into mature T-cells. Deterioration of thymus function results in an increased susceptibility for infectious diseases. Minimizing the damage to the thymus is essential for the recovery of T-cell repopulation after RT. Even small doses of the ionising radiation used for RT can accelerate thymus deterioration. Moreover, the immature T-cells residing in the thymus are one of the most radiosensitive cells in the human body. It is therefore particularly advantageous, specially incase the RT treatment is combined with immunotheray, to take the thymus into account as an OARIS. It is also advantageous to have insight into the risk score for the thymus indicative off the risk of HT occuring in the subject to be treated in response to the RT therapy.

FIG. 3 shows various options for obtaining an HT risk score for the thymus. First, prior to therapy, planning image is acquired 310 for the subject to be treated, including the thymus region. A radiological thymus parameter is determined 315 by analyzing the image. This can be done by countouring the thymus and determining its size and shape. Alternatively or additionally, the tissue composition, in particular the fat contents of the thymus can be determined, e.g. from an MRI image. Also additionally or alternatively, metabolic function or cell proliferation can be determined from a PET image using the appropriate radiotracer.

An individual patients physiological thymus score (PTS) reflecting the thymus function can now be determined 340. In principle the radiological information can be sufficient, and will yield a radiological PTS. However, the accuracy can be improved by including further patient information. For example, blood panel information including lymphocyte counts can be received as input for the PTS determination 320. In addition, a historic patient model can be used 330. Such a model provides the radiological PTS distribution in a population of healthy individuals according to age groups. As input this model received the age of the subject to be treated as input data 335.

When the subjects PST score has been determined based on the available information and models, the risk score for the occurrence of HT due to RT treatment is derived from this 350. Additionally or alternatively to the HT risk score, an indicator for the likelyhood of recovery of the immune system, and in particular of the lymphocyte population, may also be derived. Good recovery of the immune system is associated with a better likelyhood of long-term survival and better success in follow-up treatments with immunotherapy. Low chances of recovery can be an indicator for prolonged or even chronic HT which may require additional care by the treating physician.

The results of the calculations are preferably displayed 360 to the physician or RT planning technologist. Advantageously the display provides a warning, e.g. a highlighting in red, when the risk score for the thymus is above a predefined level.

Calculations of the PTS, thysmus risk score and probability for recovery may be repeated after delivery of each treatment fraction of the RT to the subject. This will allow the physician to monitor the status of the patient and make changes to the treatment when necessary.

FIGS. 4a and 4b schematically illustrate examples of displays showing risk scores for organs at risk associated with the functioning of the immune system.

FIG. 4a is a pre-treatment thymus score board 400 for three different subjects P1, P2 and P3 for which RT treatment planning needs to be done. The score board shows in the first column the baseline lymphocyte category 401 for each subject. The categories are derived from a pre-treatment blood-panel and are indicated as M, meaning medium, for each subject. For each patient the PTS has also been calculated. The PTS 402 is shown in column 2, also according to the categories L for Low, M for medium and H for high. A low score means the thymus is functioning poorly, while a high score means the thymus is functioning well. The probability for recovery of the immune system 403 is shown in a similar manner in column 3.

The score board of FIG. 4a informs the physician that P1 will not benefit from additional thymus sparing and RT planning can therefore be done with more relaxed clinical goals for this OARIS. Patients P2 and P3 will benefit from additional thymus sparing and the clinical goals for this patients should be set accordingly.

FIG. 4b shows a patient RT monitoring report 450, again for three different patients P1, P2, and P3. The first column shows the lymphocyte ratio 451 of the current lymphocyte count to the pre-treatment lymphocyte count. The second column shows the PTS ratio 452 of the current PTS to the pre-treatment PTS. As can be seen, although the ratios of the lymphocyte counts in all three patients are the same, the changes in PTS are not. The PTS provides important additional information on the status of the immune system of the subject undergoing the treatment. FIG. 4b also shows that it follows that the immune system of P2 has a very good likelihood of recovery, P3 is a high risk of prolonged HT.

Figure 5A:
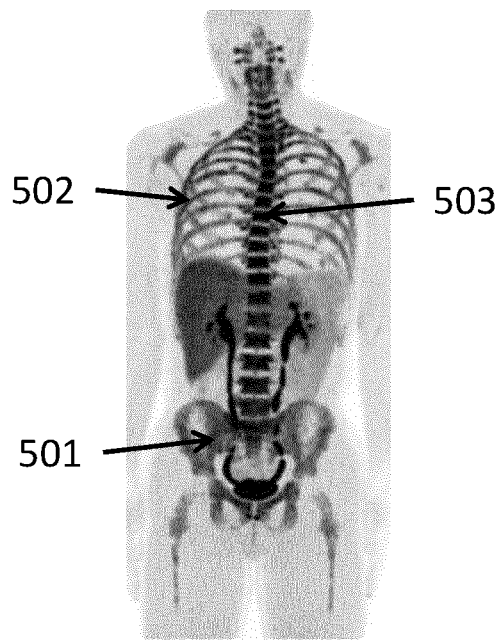
FIG. 5a schematically illustrates functional image data of a subject to be treated and FIG. 5b schematically illustrates a functional reference image.
Figure 5B:
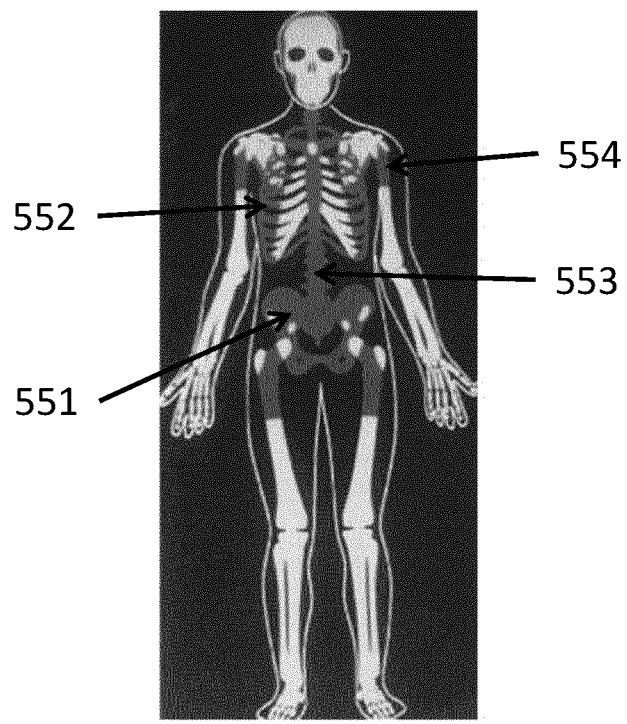

FIG. 5a schematically illustrates functional image data of a subject to be treated and FIG. 5b schematically illustrates a functional reference image.

FIG. 5a shows a functional PET image that allows a determination of the active bone marrow in the subject from the standard uptake values (SUVs) in the image. Several tracers are suitable for visualizing which areas of bone marrow active, e.g. 18-F-FDG will show metabolic turnover, and 18F-FTL provides information on cell-proliferation, as well as anti-CD8 PET tracer, allowing direct labelling of lymphocyte CD8 cells. FIG. 5a is an FLT-PET image. In this Fig. dark gray corresponds to high tracer uptake, while light gray corresponds to a low tracer uptake. As can be seen, in this subject active regions of bone marrow are located in the pelvic bones 501 and thoracic bones 502 and particularly in the spinal column 503.

Bone marrow activity decreases with age and therefore a reference model can be provided based on historic patient data by taking a statistical average per age group. FIG. 5b shows such an average for a person of a similar age as the subject of FIG. 5a. Also here dark gray represents areas of active bone marrow, while light represents inactive bone marrow. Outer contour of the reference person is indicated in white. The reference model of FIG. 5b also shows active bone marrow in the pelvic bones 551, the thoracic bones 552 and spinal column 553. The model also shows active bone marrow in the upper arms 554 that is not present in the subject of FIG. 5a.

For the active bone marrow as OARIS, the risk score can be taken as the ratio of active bone marrow within the radiation filed over the total active bone marrow both inside and outside the radiation field. Alternatively, the risk sore can be taken as the ratio of active bone marrow in the subject over the reference model for a person of the subject's age.

In another example, the risk factor can be determined for OARISSs that are large blood vessel located close to the heart as well as for heart structures. For this a personalized blood flow measurement can be obtained using e.g. Doppler echocardiography, or MRI T1 weighted perfusion imaging, and combined with a blood panel at baseline that provides the number of different white cell populations (neutrophils, lymphocytes, etc.) per unit volume. This will allow an estimation of the amount of white blood cells that will be exposed during radiation, which can be high or low relative to a standardized value. An advantage of using MRI T1 weighted perfusion imaging is that it can be obtained with a hybrid MR RT linac system, enabling measurements of personalized blood flow at each treatment fraction.

Figure 6:
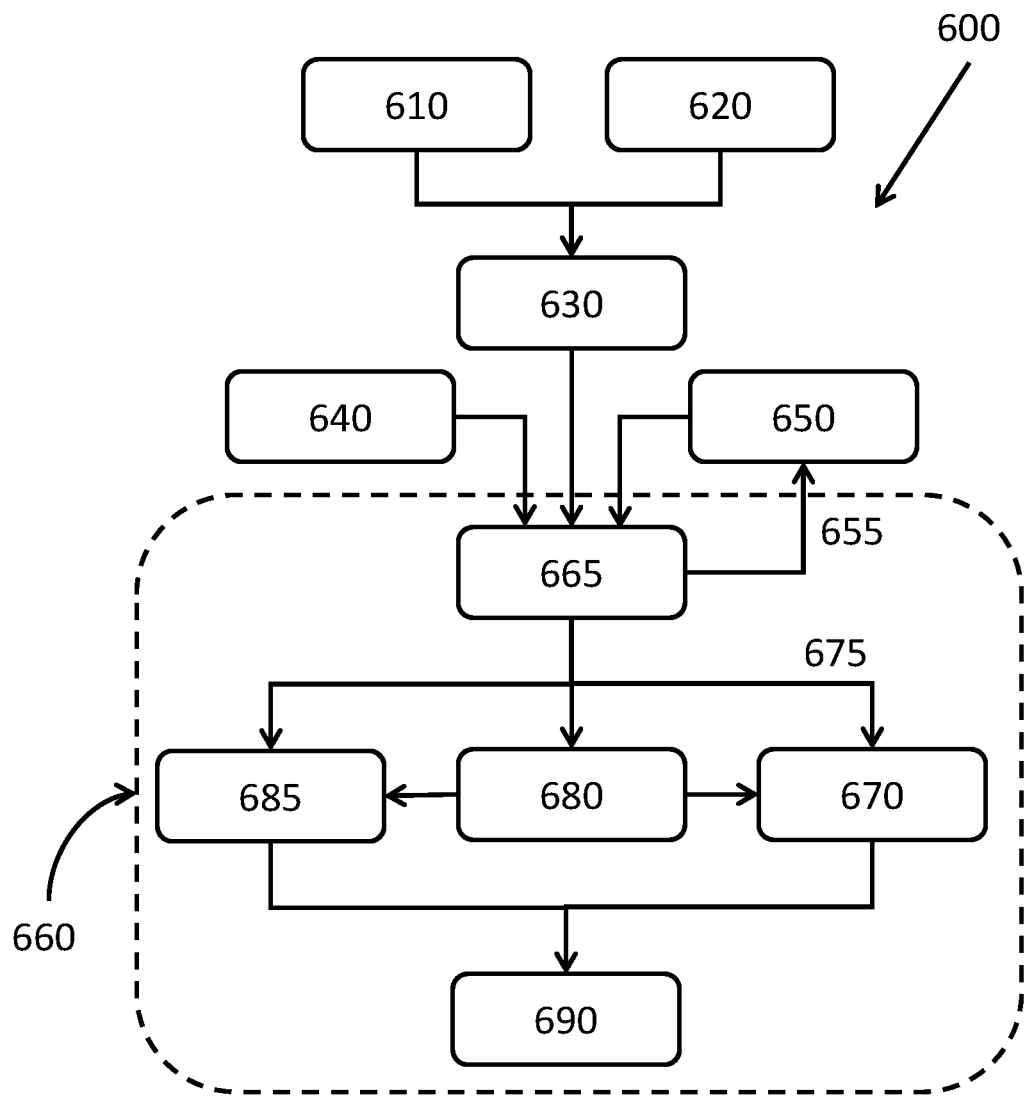
FIG. 6 schematically illustrates an example of a method for planning radiation therapy comprising calculating organ sparing probability scores for a group of possible radiation therapy treatment options.

FIG. 6 illustrates an embodiment of a method for planning radiation therapy 600 that comprises calculating organ sparing probability scores for a group of possible radiation therapy treatment options. Such a group can be a group of types of treatment where the risk score is used to select an appropriate treatment type. In the current example, however, IMRT has already been selected for the RT treatment, but a choice still needs to be made from a group of different geometric beam arrangement options.

Prior to RT planning method 600, image data relating to the subject to be treated has been acquired. The imaging data in this embodiment includes anatomical image data of a TS and one or more OARISs. The image data further comprises a planning CT image of the subject acquired prior to therapy as well as a functional FDG PET image.

As a part of the planning method, patient data relating to the subject to be treated is received 610 as well as the image data 620. The data is then processed 630 to obtain a risk score for the OARISs. In this example, a functional risk score is calculated for each OARIS using the functional image data.

After the risk score for the one or more individual OARIS have been obtained, the IMRT treatment of this exemplary embodiment is planned 660 using the risk scores. In the treatment planning, first sparing probabilities for each of the one or more OARISs are calculated 665 for each therapy option using the functional risk scores. For this purpose, the different options, in this example geometric options for beam arrangements, are provided 650. As a part of the sparing probability calculations, dosimetric features are also taken into account. Such features may be based on clinical goals for the OARISs such as mean dose, maximum dose and volume of the OARIS receiving a dose above a predefined level. In this embodiment the clinical goals are supplied at 640. The clinical goals can be prescribed and input manually by a physician or planning technologist, or the clinical goals can be received from a database, for example based on values of a standardized treatment protocol.

The sparing probability for an OARIS can be derived by calculating a sparing probability indicator. Such an indicator can be determined through several approaches, for example by calculating the number of beamlets in a therapy plan that will traverse the OARIS during treatment, the ratio of OARIS volume intersected by the beamlets and the total volume. Alternatively, an AI component comprising e.g. a Bayesian network, or neural network may be trained using historic patient data and applied to determine the current sparing probabilities. An alternative example that is personalized to the subject to be treated is the following. A sparing probability p that takes into account the probability to develop a HT may be define by the following relationship:

$$p = \frac{1}{1 + e^{-\left(a_0 + \sum_{i=1}^{n} b_i X_i + \sum_{j=1}^{m} c_j Y_j\right)}} \quad (1)$$

In this equation, $X_i$ are non-dosimetric features associated with HT, such as age of the subject, value of blood cell counts before the start of the treatment, the radiologic score of the thymus, the volume of the active bone marrow, and/or the type of chemotherapy agent in case of a combined treatment of RT with chemotherapy. Parameters $Y_j$ represent the dosimetric features of the RT treatment plan. In this equation further $a_0$ is a constant factor, $b_i$ are coefficients indicating the relative importance of each of the non-dosimetric OARISs risk factors, and $c_j$ are the coefficients indicating the relative importance of the dosimetric features $Y_j$. The coefficients $a_0$, $b_i$, and $c_j$ can be determined by fitting a logistic regression model to population data.

For the subject to be treated, the values of the non-dosimetric features $X_i$ will be known before the start of the treatment. However, different RT plan options with different dose distributions will result in different values for the dosimetric features $Y_j$. This can be expressed as follows:

$$p_k = \frac{1}{1 + e^{-\left(a_0 + \sum_{i=1}^{n} b_i X_i + \sum_{j=1}^{m} c_j Y_j^k\right)}} \quad (2)$$

In this equation k indicates the plan option, for example this can be dose distributions 1,2, . . . , k, or geometric beam arrangements 1,2, . . . , k. Dosimetric features $Y_j^k$ are the dosimetric features of specific option k and sparing probability indicator $p_k$ indicates the sparing probability specific to that option.

The dosimetric features for a dose distribution or beam arrangement can be approximated from the beam arrangements, predicted from a database of pre-calculated plans, of from a previously fully optimized plan for the patient. It is advantageous to use an approximated dose distribution or a plan predicted based on a database, since improve calculation efficiency. For these cases only the full RT plan with optimal OARIS sparing will be fully calculated and optimized.

After the risk scores have been obtained as well as the sparing probabilities, a beam arrangement is selected 670 for the IMRT. In an alternative option, in case none of the geometric beam arrangements are satisfactory, the user can return 655 to 650 to supply further alternative beam arrangements and recalculate the sparing probabilities at 665.

The preferred beam arrangement can be selected automatically 675 using predefined criteria, or the selection can be entered by the physician or planning technologist. For the purpose of reviewing the options, the OARIS risk scores along with their sparing probabilities for the various beam arrangement options are displayed 680. Using the displayed information, the physician may also decide to modify one or more of the clinical goals 685 to improve sparing for OARISs with a high risk of HT, or to make clinical goals less stringent for sparing for OARIS with a low risk of HT.

After the beam arrangement has been selected and optionally the clinical goals modified, the RT treatment plan is fully calculated and optimized 690.

Figure 7:
FIG. 7 schematically illustrates a display showing risk scores for organs at risk associated with the functioning of the immune system with sparing options for different possible radiation therapy treatment options.

FIG. 7 provides an example of a display showing risk scores for OARIS with sparing options for different possible radiation therapy treatment options.

In this example, the information is presented in the form of a data table 710. When the display is part of an interactive planning system, the table may be part of a GUI, that will allow the user to click various fields to access additional information and/or select the preferred treatment option for calculating the final treatment plan to be delivered.

The subject illustrated in 710 has a lung tumor that is located close to the vertebrae. In this subject, and FDG PET scan has shown that most of the active bone marrow is located in the thoracic vertebrae region which lies within the initial irradiation field of the RT treatment. As a result, the risk factor for the active bone marrow is high. In this subject, the size of the thymus is within the expected size for the age and baseline lymphocyte counts are normal. The resulting risk for the thymus is high.

The exemplary information shown in table 710 shows information for intensity modulated radiation therapy (IMRT) with two possible geometric beam arrangements. The rows of the table indicate the relevant OARISs, in this case there are four, bone marrow OARIS1, the thymus OARIS2, the heart chambers OARIS3 and large blood vessels OARIS4. Column 2 shows the obtained risk score 715 for each OARIS. Preferably this risk score is a functional risk score. The risk score has a value between 0 and 1 with 0 being the lowest risk and 1 the highest. The thirst column shows the sparing probability for the first IMRT beam arrangement 720 and the fourth column shows the sparing probability for the second beam arrangement 725. The sparing probability is indicated with the symbols L for low, M for medium, and H for high. Additionally or alternatively stoplight colors could be used to highlight the table with green for low, yellow for medium and red for high.

As can be seen in FIG. 7, the bone marrow OARIS1 and thymus OARIS2 have a high risk of causing HT in response to the radiation therapy, while the risk for the heart chambers and blood vessels is low. From the display, the radiation oncologist or planning technologist learns that the first beam arrangement 720 puts the bone marrow at significant risk and therefore the second beam arrangement 725 is preferred. The second beam arrangement is therefore chosen to proceed with the full calculation and optimization of the IMRT treatment plan.

Any of the method steps disclosed herein, may be recorded in the form of a computer program comprising instructions which when executed on a processor cause the processor to carry out such method steps. The instructions may be stored on a computer program product. The computer program product may be provided by dedicated hardware as well as hardware capable of executing software in association with appropriate software. When provided by a processor, the functions can be provided by a single dedicated processor, by a single shared processor, or by a plurality of individual processors, some of which can be shared. Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system, or apparatus or device, or a propagation medium. Examples of a computer-readable medium include a semiconductor or solid state memory, magnetic tape, a removable computer diskette, a random access memory "RAM", a read-only memory "ROM", a rigid magnetic disk and an optical disk. Current examples of optical disks include compact disk-read only memory "CD-ROM", compact disk-read/write "CD-R/W", Blu-Ray™ and DVD. Examples of a propagation medium are the Internet or other wired or wireless telecommunication systems.

Variations to the disclosed embodiments can be understood and effected by those skilled in the art in practicing the claimed invention, from a study of the drawings, the disclosure, and the appended claims. It is noted that the various embodiments may be combined to achieve further advantageous effects.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A method for planning radiation therapy the method comprising:
receiving patient data of a subject to be treated;
receiving image data of the subject to be treated, which image data comprises anatomical image data of one or more organs at risk associated with a functioning of an immune system;
processing the patient data and the image data to obtain a risk score for the one or more organs at risk associated with the functioning of the immune system, which risk score is indicative of a risk of hematologic toxicity in the subject to be treated in response to the radiation therapy; and
planning a radiation therapy treatment using the obtained risk score to reduce the risk of hematologic toxicity in the subject to be treated.

2. The method according to claim 1, wherein the image data of the subject further includes functional image data for the one or more organ at risk associated with the functioning of the immune system, and wherein the risk score is obtained by applying a functional model of the organs at risk.

3. The method according to claim 1, wherein the risk score is obtained by applying a model based on historic patient data.

4. The method according to claims 1, wherein the patient data comprises blood cell counts in the subject, in particular lymphocyte counts in the subject.

5. The method according to any of claims 1-4, wherein the one or more organs at risk associated with the functioning of the immune system are at least one of: a thymus, an area of active bone marrow, vertebra, a heart, heart chambers, or a large blood vessel.

6. The method according to claim 1, wherein planning a radiation therapy treatment comprises selecting a type of radiation therapy; and calculating a radiation therapy plan for the selected type of radiation therapy.

7. The method of claim 6, wherein the type of radiation therapy includes at least one of an intensity modulated radiation therapy, a volumetric modulated radiation therapy, a photon radiation therapy with a non-coplanar beam arrangement, and a proton or other particle therapy.

8. The method according to claims 1, wherein the image data further comprises anatomical image data of at least a target structure; and the method further comprises receiving one or more clinical goals for the target structure and the one or more organs at risk.

9. The method according to claim 8, wherein planning the radiation therapy treatment comprises adjusting the clinical goals using the obtained risk score.

10. The method according to claims 8, wherein planning the radiation therapy treatment comprises calculating organ sparing probability scores for the or more organs at risk associated with the functioning of the immune system for each of a group of possible radiation therapy treatment options.

11. The method according to claim 10, wherein the radiation therapy treatment options are different geometric beam arrangements in intensity modulated radiation therapy.

12. A system for planning radiation therapy comprising:
an input for receiving patient data of a subject to be treated;
an input for receiving image data of the subject to be treated, which image data comprises anatomical image data of at least one organ at risk associated with a functioning of an immune system;
a risk score calculation unit configured to process the patient data and the image data to obtain a risk score for one or more organs at risk associated with the functioning of the immune system indicative of a risk of hematologic toxicity in the subject to be treated in response to the radiation therapy; and a radiation therapy planning unit configured to select a radiation therapy plan using the obtained risk score to reduce the risk of hematologic toxicity in the subject to be treated.

13. The system according to claim 12, further comprising a display unit configured to display the risk score of the at least one organ at risk.

14. The system according to claim 13, wherein the display is further configured to display organ sparing probability scores for the organs at risk associated with the functioning of the immune system for each of a group of possible radiation therapy options.

15. An arrangement for radiation therapy planning comprising:

one or more imaging devices configured to generate image data of a subject to be treated;

a patient information database configured to store and provide patient data; and a system for planning radiation therapy comprising:

an input for receiving patient data of a subject to be treated:

an input for receiving image data of the subject to be treated, which image data comprises anatomical image data of at least one organ at risk associated with a functioning of an immune system;

a risk score calculation unit configured to process the patient data and the image data to obtain a risk score for one or more organs at risk associated with a functioning of the immune system indicative of the risk of hematologic toxicity in the subject to be treated in response to the radiation therapy; and a radiation therapy planning unit configured to select a radiation therapy plan using the obtained risk score to reduce a risk of hematologic toxicity in the subject to be treated.

* * * * *